United States Patent
Meis et al.

(10) Patent No.: US 9,227,733 B2
(45) Date of Patent: Jan. 5, 2016

(54) AUTOMATED WATER DROP MEASUREMENT AND ICE DETECTION SYSTEM

(71) Applicant: The Boeing Company, Chicago, IL (US)

(72) Inventors: Charles Steven Meis, Renton, WA (US); Erik Marc Langhofer, Seattle, WA (US)

(73) Assignee: THE BOEING COMPANY, Chicago, IL (US)

(*) Notice: Subject to any disclaimer, the term of this patent is extended or adjusted under 35 U.S.C. 154(b) by 329 days.

(21) Appl. No.: 13/732,707

(22) Filed: Jan. 2, 2013

(65) Prior Publication Data

US 2014/0184789 A1 Jul. 3, 2014

(51) Int. Cl.
| | |
|---|---|
| B64D 15/20 | (2006.01) |
| G01N 15/02 | (2006.01) |
| G01N 1/22 | (2006.01) |
| B64D 15/22 | (2006.01) |
| G08B 19/02 | (2006.01) |
| G01N 1/28 | (2006.01) |

(52) U.S. Cl.
CPC ............. *B64D 15/20* (2013.01); *G01N 1/2202* (2013.01); *G01N 1/2214* (2013.01); *G01N 15/0227* (2013.01); *B64D 15/22* (2013.01); *G01N 2001/2833* (2013.01); *G08B 19/02* (2013.01)

(58) Field of Classification Search
CPC ................................ G01N 21/84; B64D 15/20
USPC ........................................................ 348/135
See application file for complete search history.

(56) References Cited

U.S. PATENT DOCUMENTS

| | | | |
|---|---|---|---|
| 6,759,962 B2 * | 7/2004 | Severson et al. ............... 340/580 |
| 2007/0046478 A1 * | 3/2007 | Crisman ........................ 340/580 |
| 2007/0074415 A1 | 4/2007 | Gagnon |
| 2010/0020170 A1 * | 1/2010 | Higgins-Luthman et al. .............................. 348/135 |
| 2012/0085868 A1 * | 4/2012 | Barnes ........................ 244/134 F |
| 2014/0035803 A1 * | 2/2014 | Melkers ........................ 345/156 |

FOREIGN PATENT DOCUMENTS

| | | |
|---|---|---|
| EP | 1396425 A1 | 3/2004 |
| EP | 2277776 A2 | 1/2011 |

OTHER PUBLICATIONS

Extended European Search Report, dated Aug. 11, 2014, regarding Application No. EP13196534.5, 6 pages.
Brown, "A Technique for Measuring Precipitation Particles from Aircraft," Journal of Meteorology, University of Chicago, vol. 15, Oct. 1958, pp. 462-466.

* cited by examiner

*Primary Examiner* — William C Vaughn, Jr.
*Assistant Examiner* — Jerry Jean Baptiste
(74) *Attorney, Agent, or Firm* — Yee & Associates, P.C.

(57) ABSTRACT

A method and apparatus for detecting an icing condition. The apparatus comprises a sensor system and an icing condition detector. The sensor system is configured to collect drops of water from air on an exterior of an aircraft and generate a number of images of the drops of water collected. The icing condition detector is configured to detect a presence of a number of types of icing conditions for the aircraft using the number of images from the sensor.

14 Claims, 10 Drawing Sheets

AUTOMATED WATER DROP MEASUREMENT AND ICE DETECTION SYSTEM

BACKGROUND INFORMATION

1. Field

The present disclosure relates generally to detecting icing conditions and, in particular, to detecting icing conditions for an aircraft. Still more particularly, the present disclosure relates to detecting supercooled drops of water, including supercooled large drops (SLD) for aircraft.

2. Background

In aviation, icing on an aircraft may occur when atmospheric conditions lead to the formation of ice on the surfaces of the aircraft. Further, this ice also may occur within the engine. Ice forming on the surfaces of the aircraft, on inlets of an engine, and on other locations is undesirable and potentially unsafe for operating the aircraft.

Icing conditions may occur when drops of supercooled liquid water are present. In these illustrative examples, water is considered to be supercooled when the water is cooled below the stated freezing point for water but is still in a liquid form. Icing conditions may be characterized by the size of the drops, the liquid water content, air temperature, and other parameters. These parameters may affect the rate and extent at which ice forms on an aircraft.

When icing occurs, the aircraft does not operate as desired. For example, ice on the wing of an aircraft will cause the aircraft to stall at a lower angle of attack and have an increased drag.

Aircraft may have mechanisms to prevent icing, remove ice, or some combination thereof to handle these icing conditions. For example, aircraft may include icing detection, prevention, and removal systems. Ice may be removed using deicing fluid, infrared heating, and other suitable mechanisms.

Aircraft may be certified for operation during different types of icing conditions. Some aircraft may be certified to operate in normal icing conditions, but not those that include supercooled large drops. Currently used sensor systems are unable to differentiate between normal and supercooled large drop icing conditions. Therefore, it would be desirable to have a method and apparatus that takes into account at least some of the issues discussed above, as well as other possible issues.

SUMMARY

In one illustrative embodiment, an apparatus comprises a sensor system and an icing condition detector. The sensor system is configured to collect drops of water from air on an exterior of an aircraft and generate a number of images of the drops of water collected. The icing condition detector is configured to detect a presence of a number of types of icing conditions for the aircraft using the number of images from the sensor.

In another illustrative embodiment, an icing condition detection system comprises a group of sensor units and an icing condition detector. The group of sensor units is configured to generate information about a number of types of icing conditions outside of an aircraft. A sensor unit in the group of sensor units comprises a number of probes configured to collect the drops of water from the air on the exterior of the aircraft and a camera system configured to generate the number of images of the drops of water collected by the number of probes. The icing condition detector is configured to detect a presence of the number of types of icing conditions for the aircraft using the number of images from the camera system.

In yet another illustrative embodiment, a method for detecting an icing condition is provided. Drops of water are collected from air on an exterior of an aircraft. A number of images of the drops of water collected is generated. A determination is made as to whether a number of types of icing conditions for the aircraft is present using the number of images from the sensor system.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account a number of different considerations. For example, the different illustrative embodiments recognize and take into account that currently used systems for detecting icing conditions on an aircraft are unable to detect all of the different types of icing conditions that may occur. For example, the different illustrative embodiments recognize and take into account that as the size of the drops of water increase, currently used sensors may not detect icing caused by those drops of water. The different illustrative embodiments recognize and take into account that the locations at which different sizes of drops will collide with an airfoil during operation of an aircraft change depending on the size of the drops.

The illustrative embodiments recognize and take into account that it is desirable to detect different types of icing conditions that may be caused by different sizes of drops of water. In particular, the illustrative embodiments recognize and take into account that it may be desirable to detect drops of supercooled liquid water. These drops may take the form of supercooled large drops (SLD).

Thus, the illustrative embodiments provide a method and apparatus for detecting different types of icing conditions. In one illustrative embodiment, a method and apparatus are present for detecting an icing condition. Drops of water are collected from the air on the exterior of an aircraft. A number of images of the drops of water collected are generated. A determination is made as to whether a number of types of icing conditions for the aircraft is present using the images. In these illustrative examples, the phrase "number of" when used with reference with items mean one or more items. For example, number of images is one or more images.

Figure 1:
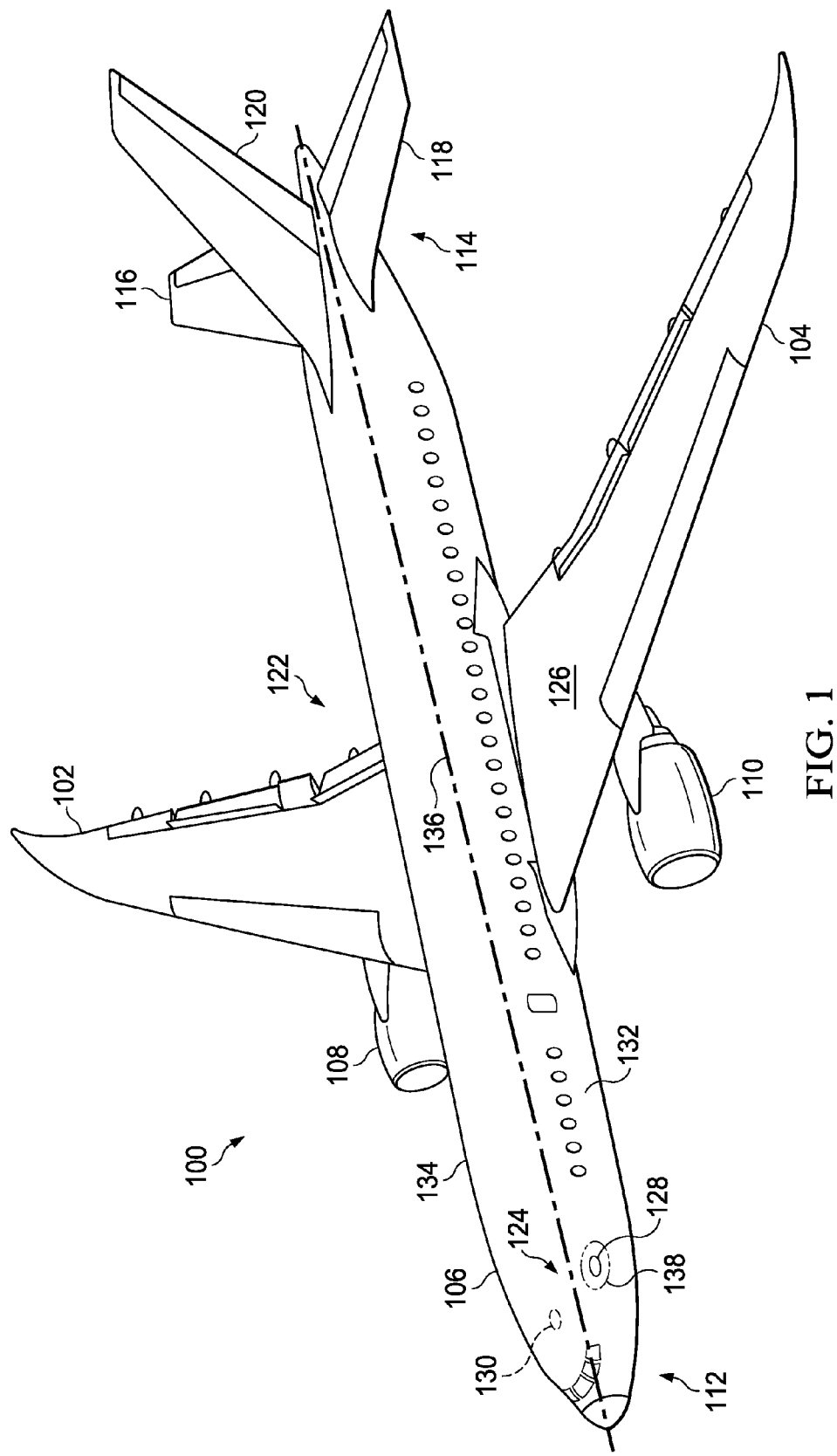
FIG. 1 is an illustration of an aircraft in accordance with an illustrative embodiment.

With reference now to the figures and, in particular, with reference to FIG. 1, an illustration of an aircraft is depicted in accordance with an illustrative embodiment. In this illustrative example, aircraft 100 has wing 102 and wing 104 attached to fuselage 106. Aircraft 100 also includes engine 108 attached to wing 102 and engine 110 attached to wing 104.

Fuselage 106 has nose section 112 and tail section 114. Nose section 112 is the forward part of aircraft 100, while tail section 114 is the aft part of aircraft 100. Horizontal stabilizer 116, horizontal stabilizer 118, and vertical stabilizer 120 are attached to tail section 114 of fuselage 106.

Aircraft 100 is an example of a vehicle in which icing condition detection system 122 may be implemented. In this illustrative example, icing condition detection system 122 includes sensor units 124 located on surface 126 of aircraft 100.

In this particular example, sensor units 124 include sensor unit 128 and sensor unit 130. Sensor unit 128 is located on side 132 of aircraft 100. Sensor unit 130 is located on side 134 of aircraft 100. In this illustrative example, sensor unit 134 is substantially opposite of sensor unit 128 and is shown in phantom. In one illustrative example, sensor unit 128 and sensor unit 130 may be located substantially at horizontal center line 136 in aircraft 100. A more detailed illustration of sensor unit 128 in location 138 on fuselage 106 is described in more detail below.

In these illustrative examples, sensor units 124 are configured to collect drops of water that may be present in the air around surface 126 of aircraft 100. These drops of water may be analyzed to determine a presence of a number of types of icing conditions. In these illustrative examples, sensor units 124 may generate images of the drops of water for analysis. The analysis may indicate whether the drops of water are frozen drops of water, the size of the drops of water, and other suitable information that may be used to identify a presence of a number of types of icing conditions.

In these illustrative examples, these icing conditions may occur at different altitudes and temperatures that cause the formation of ice on aircraft 100. For example, icing conditions may be present at an altitude from about sea level to about 30,000 feet when the temperature is from about −40 degrees Celsius to about 0 degrees Celsius. Of course, other altitudes and temperatures may be present at which ice may be formed from water that contacts surface 126 of aircraft 100. Icing conditions also may be present when the liquid water content in the drops is from about 0.4 to about 2.8 grams/cubic meter at the altitude and temperature range described above.

In particular, the number of types of icing conditions may include a first type of icing condition and a second type of icing condition. In these illustrative examples, the first type of icing condition and the second type of icing condition are caused by drops of water of different sizes. Although the altitude, temperature, and liquid water content ranges may be the same, one difference between the first and second types of icing conditions is the drop size.

In the illustrative examples, the first type of icing condition may be referred to as a normal icing condition. The second type of icing condition may be referred to as a supercooled large drop icing condition.

In these illustrative examples, the first type of icing condition may be present when the size of the drops is from about 0.00465 millimeters in diameter to about 0.111 millimeters in diameter. Drops with these sizes may be referred to as normal drops. The second type of icing condition may be present when the size of the drops includes drops that have a diameter greater than about 0.111 millimeters. Drops having a size greater than about 0.111 millimeters may be referred to as large drops and, in particular, may be called supercooled large drops under the altitude, temperature, and liquid water content conditions described above. For example, the drops may have a diameter of a range from about 0.112 millimeters to about 2.2 millimeters. In addition, the second type of icing condition may include drops that are 0.111 millimeters or less when drops greater than 0.111 millimeters are present.

As depicted, sensor units 124 are configured to detect drops of water in a first number of sizes. Further, sensor units 124 also are configured to detect drops of water having a second number of sizes. These drops of water may be in a liquid state, a frozen state, or some combination thereof. In these illustrative examples, the first number of sizes is smaller than the second number of sizes.

For example, the first number of sizes may be from about 0.00465 millimeters in diameter to about 0.111 millimeters in diameter. The second number of sizes may be from about 0.112 millimeters to about 2.2 millimeters in diameter. The second number of sizes of the drops of water may be drops of water that are considered to be drops of supercooled water. These drops of supercooled water may be supercooled large drops.

The illustration of sensor units 124 are not meant to imply limitations to the manner in which sensor units may be implemented in other illustrative examples for aircraft 100 and other aircraft or vehicles in which detection of icing conditions is desired. For example, other numbers of sensor units may be used in addition to sensor unit 128 and sensor unit 130 in sensor units 124. For example, in other illustrative examples, five sensor units, twelve sensor units, or some other suitable number of sensor units may be employed.

These sensor units also may be placed in other locations such as on vertical stabilizer 120, on engine 110, and other suitable locations. As another example, sensor units 124 also may be positioned above horizontal center line 136 on aircraft 100.

Figure 2:
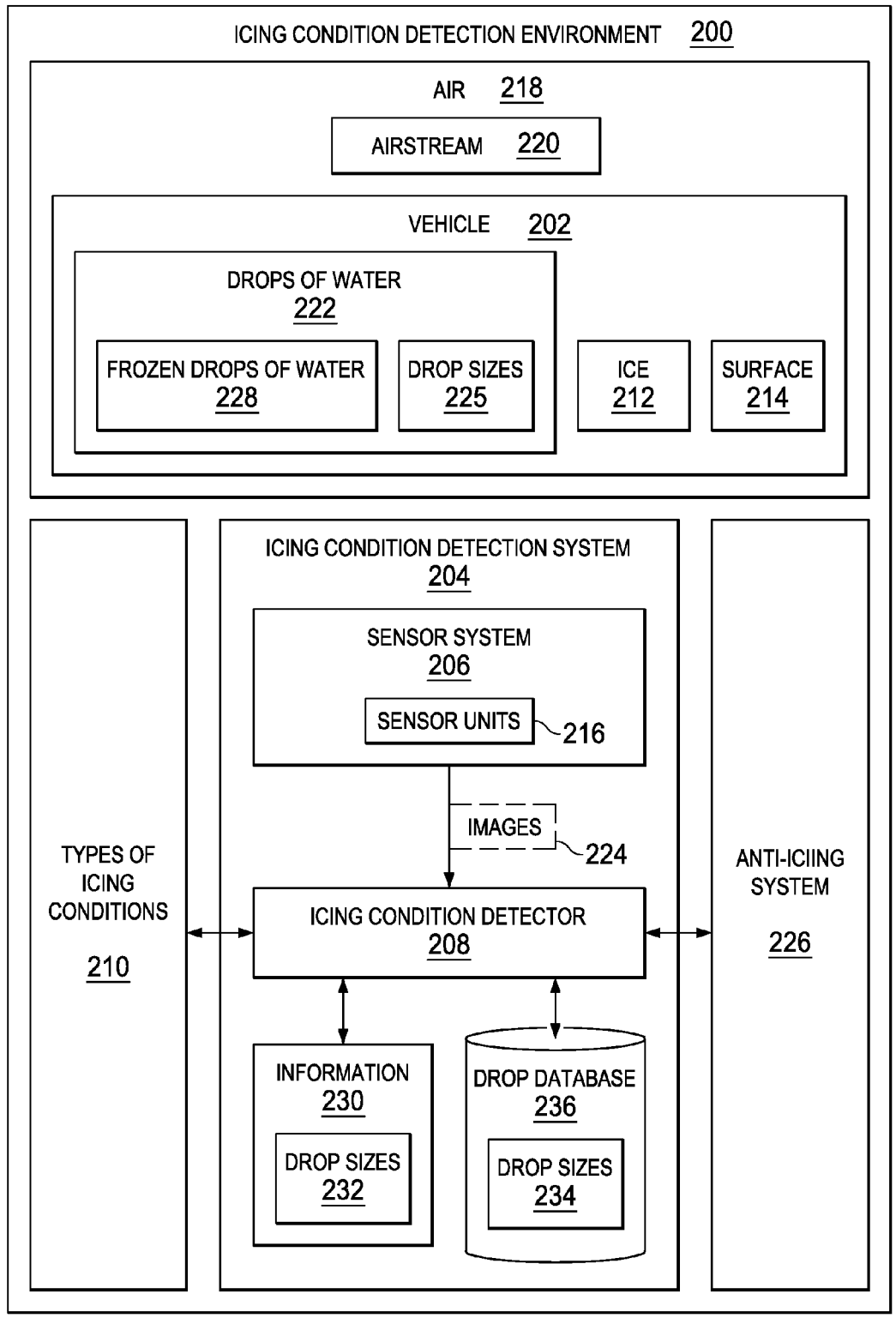
FIG. 2 is an illustration of a block diagram of an icing condition detection environment in accordance with an illustrative embodiment.

Turning now to FIG. 2, an illustration of a block diagram of an icing condition detection environment is depicted in accordance with an illustrative embodiment. Icing condition detection environment 200 is an environment in which ice detection may be performed for vehicle 202. In this illustrative example, vehicle 202 may be aircraft 100 in FIG. 1.

Icing condition detection system 204 may be associated with vehicle 202. When one component is "associated" with another component, the association is a physical association in these depicted examples. For example, a first component, icing condition detection system 204, may be considered to be associated with a second component, vehicle 202, by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

In this illustrative example, icing condition detection system 204 includes sensor system 206 and icing condition detector 208. Icing condition detection system 204 is configured to detect a number of types of icing conditions 210.

In particular, icing condition detection system 204 may be configured to detect whether the number of types of icing conditions 210 are present where ice 212 may be formed on surface 214 of vehicle 202. In this illustrative example, vehicle 202 may take a number of different forms including aircraft 100 in FIG. 1.

In the illustrative examples, sensor system 206 is a hardware system and may include software. In these illustrative examples, sensor system 206 is comprised of a number of sensor units 216.

Each sensor unit in the number of sensor units 216 is associated with surface 214 of vehicle 202. In particular, number of sensor units 216 may be in locations that are exposed to air 218. In particular, the number of sensor units 216 may be positioned to be within airstream 220 in air 218 around vehicle 202.

Sensor system 206 is configured to detect drops of water 222. In particular, the number of sensor units 216 in sensor system 206 may be configured to collect drops of water 222 from air 218 on the exterior of vehicle 202. A number of drops of water 222 may be in a liquid state, a frozen state, or some combination thereof. In other words, the number of drops of water 222 may include frozen drops of water 228. Drops of water 222 may freeze during the collection process performed by sensor system 206 to collect drops of water 222 for analysis.

Additionally, sensor system 206 is configured to generate a number of images 224 of drops of water 222 collected by sensor system 206. The number of images 224 of drops of water 222 may be analyzed by icing condition detector 208.

As depicted, icing condition detector 208 is configured to detect a presence of the number of types of icing conditions 210 for vehicle 202 using the number of images 224 generated by sensor system 206. Icing condition detector 208 may be implemented using hardware, software, or some combination thereof. When software is used, the operations performed by icing condition detector 208 may be implemented in program code configured to run on a processor unit. When hardware is employed, the hardware may include circuits that operate to perform the operations in icing condition detector 208.

In the illustrative examples, the hardware may take the form of a circuit system, an integrated circuit, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. Additionally, the processes may be implemented in organic components integrated with inorganic components and/or may be comprised entirely of organic components excluding a human being. For example, the processes may be implemented as circuits in organic semiconductors.

In one illustrative example, icing condition detector 208 is configured to generate information 230 about drops of water 222 from images 224. In particular, information 230 may include drop sizes 232 for drops of water 222. Drop sizes 232 identified for drops of water 222 may be compared to drop sizes 234 in drop database 236. Drop sizes 234 in drop database 236 are sizes for drops of water for different icing conditions in types of icing conditions 210.

In these illustrative examples, drop sizes 232 may be identified from empirical data. The empirical data may be generated from using drops with known sizes that are collected by sensor system 206. For example, the measurements may be images of drops of water 222 collected by sensor system 206 from air 218. Drops of water 222 have drop sizes 225, which are known when generating drop database 236.

For example, drop sizes 232 for drops of water 222 collected on devices such as probes may be different from drops sizes 225 for drops of water 222 in air 218. In other words, drops of water 222 in the air may have a different size from when drops of water 222 adhere or land on a surface of a device, such as a probe. Drop sizes 232 may be correlated to drop sizes 225 when drop sizes 225 are known. This information may be used to create drop database 236 for identifying types of icing conditions 210.

The comparison of drop sizes 232 for drops of water 222 to drop sizes 234 in drop database 236 may be performed in substantially real time. In other words, as icing condition detector 208 detects drops of water 222 with drop sizes 232, drop sizes 232 are compared to drop sizes 234 in drop database 236 as fast as possible without intentional delay. In this manner, information 230 may be generated in substantially real time.

The comparison of drop sizes 232 for drops of water 222 to drop sizes 234 in drop database 236 may be used to identify a presence of a number of types of icing conditions 210 around vehicle 202. In particular, the type of icing condition or types of icing conditions in types of icing conditions 210 may be identified from this comparison.

Additionally, icing condition detector 208 is configured to perform an operation in response to detecting a presence of one or more types of icing conditions 210. In particular, types of icing conditions 210 may include a first type of icing condition and a second type of icing condition as described above.

The operation that may be performed by icing condition detector 208 may include activating anti-icing system 226. In this illustrative example, anti-icing system 226 may take a number of different forms. For example, anti-icing system 226 may include at least one of an infrared heater, an electrical resistive heater, a de-icer boot, and other suitable types of anti-icing devices. Anti-icing system 226 may be used for at least one of reducing the formation of icing, preventing the formation of ice, and removing ice from the surfaces of vehicle 202 in these illustrative examples.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C or item B and item C. In other examples, "at least one of" may be, for example, without limitation, two of item A, one of item B, and ten of item C; four of item B and seven of item C; and other suitable combinations.

Additionally, icing condition detector 208 also may perform other operations in place of or in addition to activating anti-icing system 226. For example, the other operations may include at least one of generating an alert, generating a log entry, sending a report, or other suitable types of operations.

In this manner, icing condition detection system 204 is configured to detect different types of icing conditions 210. In these illustrative examples, icing condition detection system 204 may provide for automated, real time water drop measurement and for ice detection based on a number of types of icing conditions 210 that may be identified.

Figure 3:
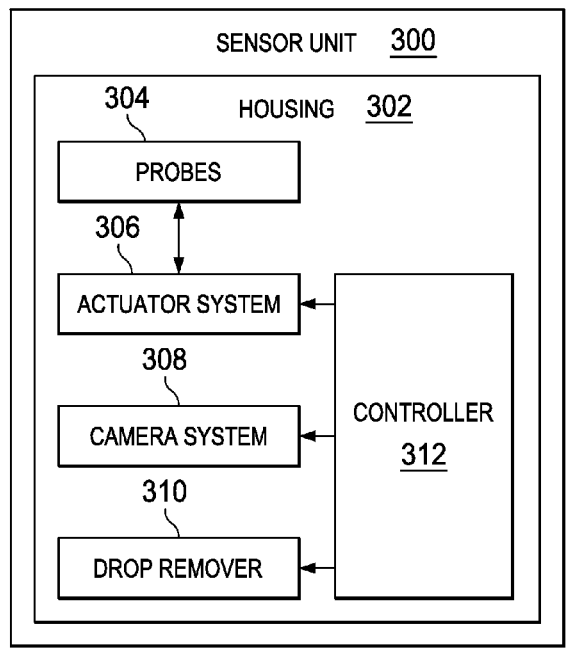
FIG. 3 is an illustration of a block diagram of a sensor unit in accordance with an illustrative embodiment.

Turning now to FIG. 3, an illustration of a block diagram of a sensor unit is depicted in accordance with an illustrative embodiment. Sensor unit 300 is an example of one implementation of a sensor unit in sensor units 216 for sensor system 206 in FIG. 2.

Sensor unit 300 includes a number of different types of components in this illustrative example. As depicted, sensor unit 300 includes housing 302, probes 304, actuator system 306, camera system 308, drop remover 310, and controller 312.

Housing 302 is a physical structure in which the other components in sensor unit 300 may be associated. In particular, housing 302 may contain or hold the other components in sensor unit 300.

In these illustrative examples, housing 302 may take a number of different forms. For example, housing 302 may have a shape such as a cylinder, a cube, a cuboid, a frustum, and other suitable shapes. Housing 302 may be comprised of one or more different types of materials. For example, housing 302 may be comprised of at least one of a metal, a plastic, aluminum, titanium, a composite material, and other suitable types of materials.

Probes 304 are physical structures configured to collect drops of water from the air around the vehicle. In these illustrative examples, probes 304 may extend into the air on the exterior of the vehicle and retract out of the air on the exterior of the vehicle to collect drops of water that may be present in the air around the exterior of the vehicle. In particular, probes 304 may extend into the air on the exterior of the vehicle from the housing and retract out of the air on the exterior of the vehicle into the housing.

Actuator system 306 is configured to move probes 304 to extend into the air and retract from the air. In other words, actuator system 306 may cause probes 304 to move out of housing 302 and back into housing 302. In particular, the movement of probes 304 may be such that only a portion of probes 304 are extended into the air outside of housing 302 while another portion of probes 304 are retracted out of the air inside of housing 302.

Actuator system 306 is a hardware system and may be implemented using a number of different types of actuators. For example, actuator system 306 may include components selected from a motor system such as at least one of an electric motor, a pneumatic motor, and other suitable types of components.

Camera system 308 is a hardware system and is configured to generate images of drops of water that may be collected on probes 304. In particular, camera system 308 may generate images of the drops of water when on the portion of probes 304 that are located within housing 302.

Camera system 308 may be implemented using one or more cameras. In these illustrative examples, camera system 308 may be implemented using visible light cameras. When camera system 308 includes one or more visible light cameras, camera system 308 may include a light source such as a light emitting diode or a flash. This light source provides light for images of drops of water taken by camera system 308 in conditions where the amount of ambient light is insufficient for generating images for analysis. For example, probes 304 may be operated during a night flight of an aircraft with sensor unit 300. The light or flash may be needed to generate images of drops of water captured by probes 304 in this example.

In other illustrative examples, other types of camera systems may be used. For example, camera system 308 may include an infrared camera.

Drop remover 310 is a hardware system and is configured to remove frozen, liquid, or both frozen and liquid drops of water that may be on probes 304. The removal of the frozen drops of water may occur after camera system 308 has generated the images. Drop remover 310 removes frozen drops of water on probes 304 prior to probes 304 being extended back into the air on the exterior of the vehicle outside of housing 302 in these illustrative examples.

Drop remover 310 may be implemented using a number of different types of de-icing systems. For example, drop remover 310 may be a heater configured to melt any drops of water that are frozen on probes 304. This heater may also be configured to evaporate the drops of water on probes 304 that are not yet frozen. Additionally, drop remover 310 may be a mechanical structure that scrapes frozen drops of water off of probes 304. In still other illustrative examples, drop remover 310 may scrape liquid drops of water off of probes 304. In other words, drop remover 310 may be a de-icing system, a mechanical drop removal system, or a combination thereof.

Controller 312 is a hardware device configured to control the operation of sensor unit 300. In these illustrative examples, controller 312 may be implemented as a circuit and may be an integrated circuit, a processor unit, a programmable logic array, an application specific integrated circuit, or some other suitable type of hardware.

As depicted, controller 312 may control the operation of actuator system 306 to move probes 304 into and out of housing 302. Further, controller 312 also may be configured to control the operation of camera system 308 to generate images of drops of water on probes 304. Controller 312 also may be configured to control the operation of drop remover 310 to remove frozen drops of water or other ice from probes 304 prior to probes 304 being moved back outside of housing 302 to collect additional drops of water.

The illustration of icing condition detection environment 200 and the different components in icing condition detection environment 200 in FIG. 2 and FIG. 3 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although icing condition detector 208 is shown as a separate component from sensor system 206, icing condition detector 208 may be distributed in sensor units 216 in addition to being a separate component or in place of being a separate component. Icing condition detector 208 may be located in a camera system, a housing, a computer system, or in some other suitable location in aircraft 100. In still other illustrative examples, sensor system 206 may include other types of sensors configured to detect the presence of ice 212 on surface 214 of vehicle 202, or to detect types of icing conditions 210 that may be present around vehicle 202.

In another illustrative example, vehicle 202 may take other forms other than aircraft 100. For example, vehicle 202 may be selected from one of, for example, without limitation, a personnel carrier, a tank, a train, an automobile, a bus, a spacecraft, a surface ship, and other suitable vehicles.

Figure 4:
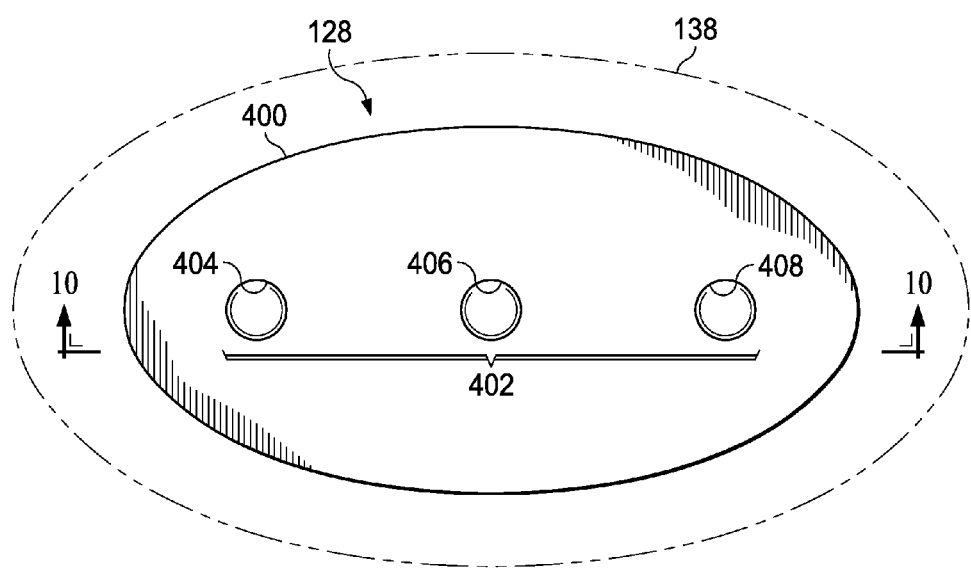
FIG. 4 is an illustration of a sensor unit on an aircraft in accordance with an illustrative embodiment.

Turning now to FIG. 4, an illustration of a sensor unit on an aircraft is depicted in accordance with an illustrative embodiment. As depicted, a more detailed illustration of sensor unit 128 at location 138 in FIG. 1 is shown.

In this view, sensor unit 128 has housing 400, which is substantially flush to surface 126 of fuselage 106 in aircraft 100. As depicted, housing 400 includes ports 402. In particular, ports 402 include port 404, port 406, and port 408.

In these illustrative examples, ports 402 provide an ability for probes (not shown) to extend from housing 400 to the exterior of aircraft 100 and to retract into housing 400 into the interior of aircraft 100. These probes may extend and retract to collect drops of water in these illustrative examples.

Although the components in FIG. 4 are shown in a particular configuration, other configurations of housing 400 and ports 402 may be implemented in an illustrative embodiment. The design of sensor unit 128 may be based on unique aircraft configurations in some illustrative examples.

Figure 5:
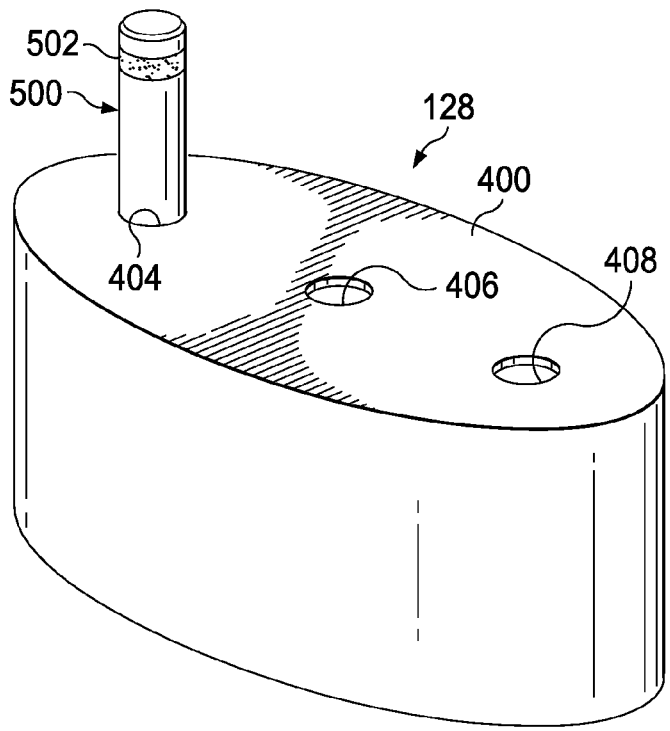
FIG. 5 is an illustration of a sensor unit in accordance with an illustrative embodiment.

Turning now to FIG. 5, an illustration of a sensor unit is depicted in accordance with an illustrative embodiment. In this example, probe 500 extends from port 404. Probe 500 may collect drops of water from air around aircraft 100 when in this extended state on the exterior of housing 400 and aircraft 100.

As depicted, probe 500 has viscous portion 502. Viscous portion 502 may be a coating on the surface of probe 500, an attachment to probe 500, or attached to probe 500 in some other suitable fashion. Viscous portion 502 may be comprised of a different type of material than probe 500. For example, viscous portion 502 of probe 500 may be comprised of a smooth but erosion-resistant material such as silicon rubber, polytetrafluoroethylene, an oily or waxy resin, or other suitable types of material. The material selected for viscous portion 502 of probe 500 may be selected such that viscous portion 502 collects drops of water.

In these illustrative examples, viscous portion 502 of probe 500 is configured such that all of viscous portion 502 may retract into housing 400 through port 404. In this manner, viscous portion 502 with drops of water may be photographed and images generated may be analyzed by sensor unit 128.

Although the depicted example shows viscous portion 502 as a small portion of probe 500, viscous portion 502 may be larger depending on the particular implementation. For example, viscous portion 502 may be configured to cover the entire surface of probe 500. In still other illustrative examples, viscous portion 502 of probe 500 may be smaller than depicted in this figure.

Figure 6:
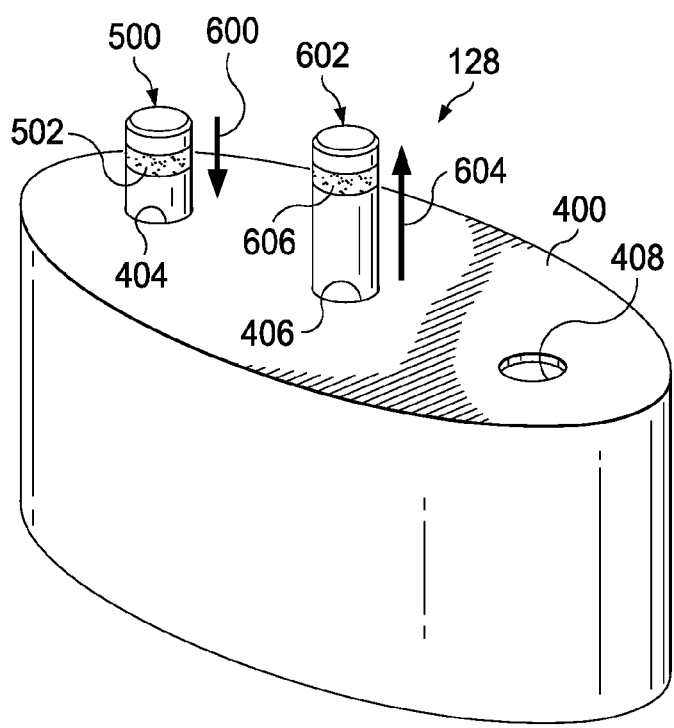
FIG. 6 is another illustration of a sensor unit in accordance with an illustrative embodiment.

Turning now to FIG. 6, another illustration of a sensor unit is depicted in accordance with an illustrative embodiment. In this view, probe 500 moves in the direction of arrow 600 to retract into housing 400 through port 404. Additionally, probe 602 moves in the direction of arrow 604 to extend outwards to the exterior of housing 400 through port 406.

In this illustrative example, probe 602 has viscous portion 606. Viscous portion 606 of probe 602 is similar to viscous portion 502 of probe 500. Viscous portion 606 is comprised of a material configured to collect drops of water on the surface of viscous portion 606.

As depicted, viscous portion 606 of probe 602 is configured such that all of viscous portion 606 may retract into housing 400 through port 406. In this manner, viscous portion 606 with drops of water may be photographed and analyzed by sensor unit 128. In some illustrative examples, viscous portion 606 may be smaller or larger than shown in this figure, depending on the particular implementation.

Figure 7:
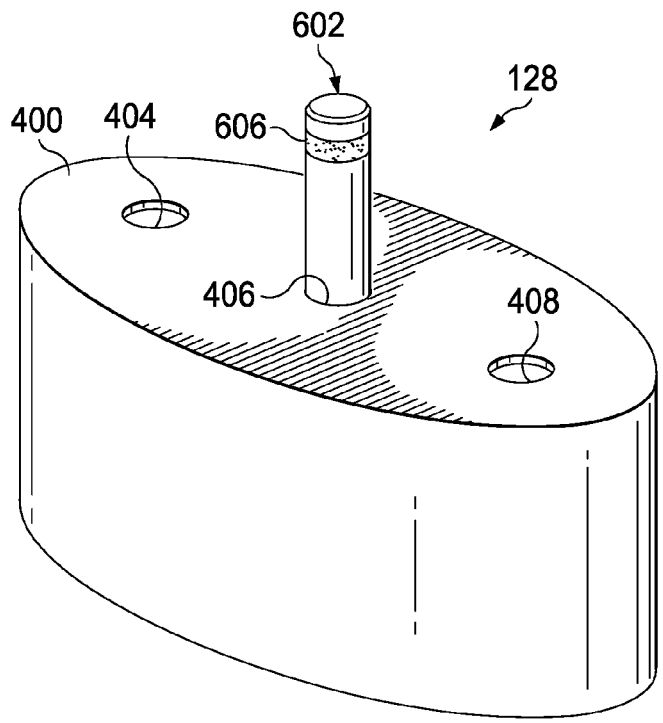
FIG. 7 is another illustration of a sensor unit in accordance with an illustrative embodiment.

Next, in FIG. 7, another illustration of a sensor unit is depicted in accordance with an illustrative embodiment. In this view, probe 602 is shown in a fully extended state outside of housing 400 and probe 500 has been fully retracted into the interior of housing 400.

Figure 8:
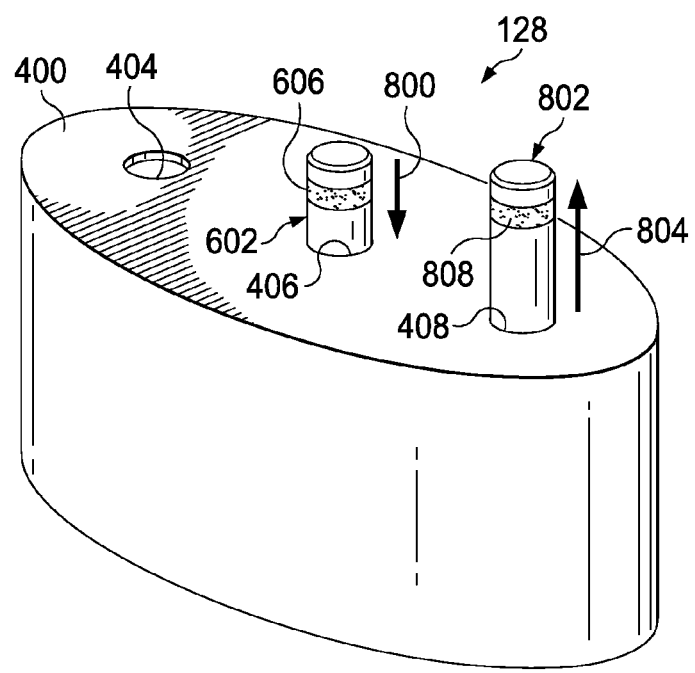
FIG. 8 is yet another illustration of a sensor unit in accordance with an illustrative embodiment.

With reference now to FIG. 8, yet another illustration of a sensor unit is depicted in accordance with an illustrative embodiment. In this example, probe 602 moves in the direction of arrow 800 to retract into the interior of housing 400 through port 406. Probe 802 moves in the direction of arrow 804 to extend outwards to the exterior of housing 400 through port 408.

As depicted, probe 802 has viscous portion 808. Viscous portion 808 of probe 802 is similar to viscous portion 502 of probe 500 and viscous portion 606 of probe 602. Viscous portion 808 is comprised of a material configured to collect drops of water on the surface of viscous portion 808.

As depicted, viscous portion 808 of probe 802 is configured such that all of viscous portion 808 may retract into housing 400 through port 408. In this manner, viscous portion 808 with drops of water may be photographed and analyzed by sensor unit 128. In some illustrative examples, viscous portion 808 may be smaller or larger than shown in this figure, depending on the particular implementation.

Figure 9:
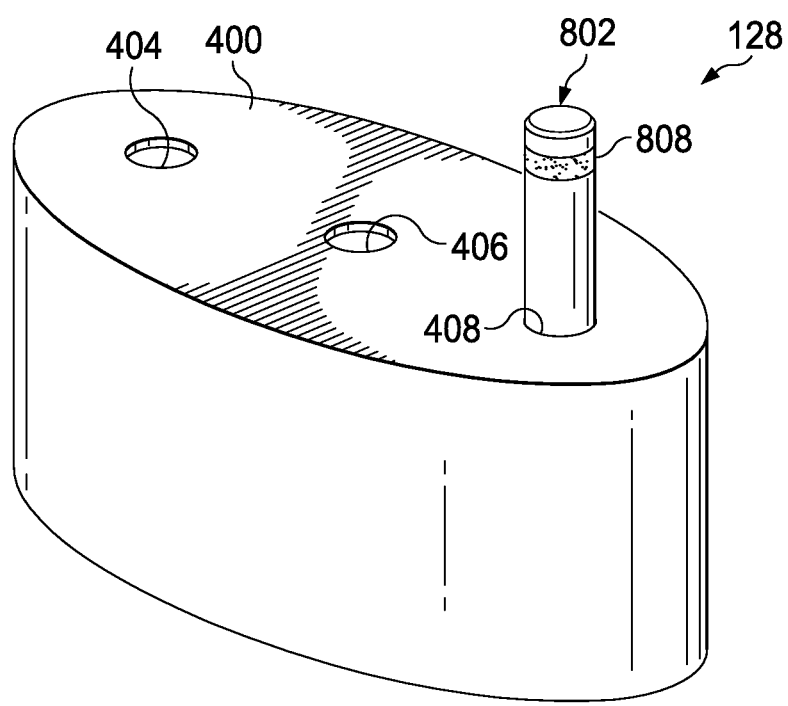
FIG. 9 is another illustration of a sensor unit in accordance with an illustrative embodiment.

In FIG. 9, another illustration of a sensor unit is depicted in accordance with an illustrative embodiment. In this illustrative example, probe 802 is shown as being fully extended on the exterior of housing 400 and probe 602 has been fully retracted into the interior of housing 400.

In the illustrative examples depicted in FIGS. 4-9, probes, such as probe 500, probe 602, and probe 802, may move in a manner such that one of the probes may always be extended to collect drops of water when the sensor unit 128 is used to detect a presence of a number of types of icing conditions. In some examples, a first probe such as probe 500 may be fully retracted before a second probe, such as probe 602, is extended. In other words, when viscous portion 502 of probe 500 reaches the interior of housing 400 in sensor unit 128 to be analyzed, probe 602 with viscous portion 606 may be extended. In other illustrative examples, more than one probe may be extended from housing 400 substantially concurrently.

Figure 10:
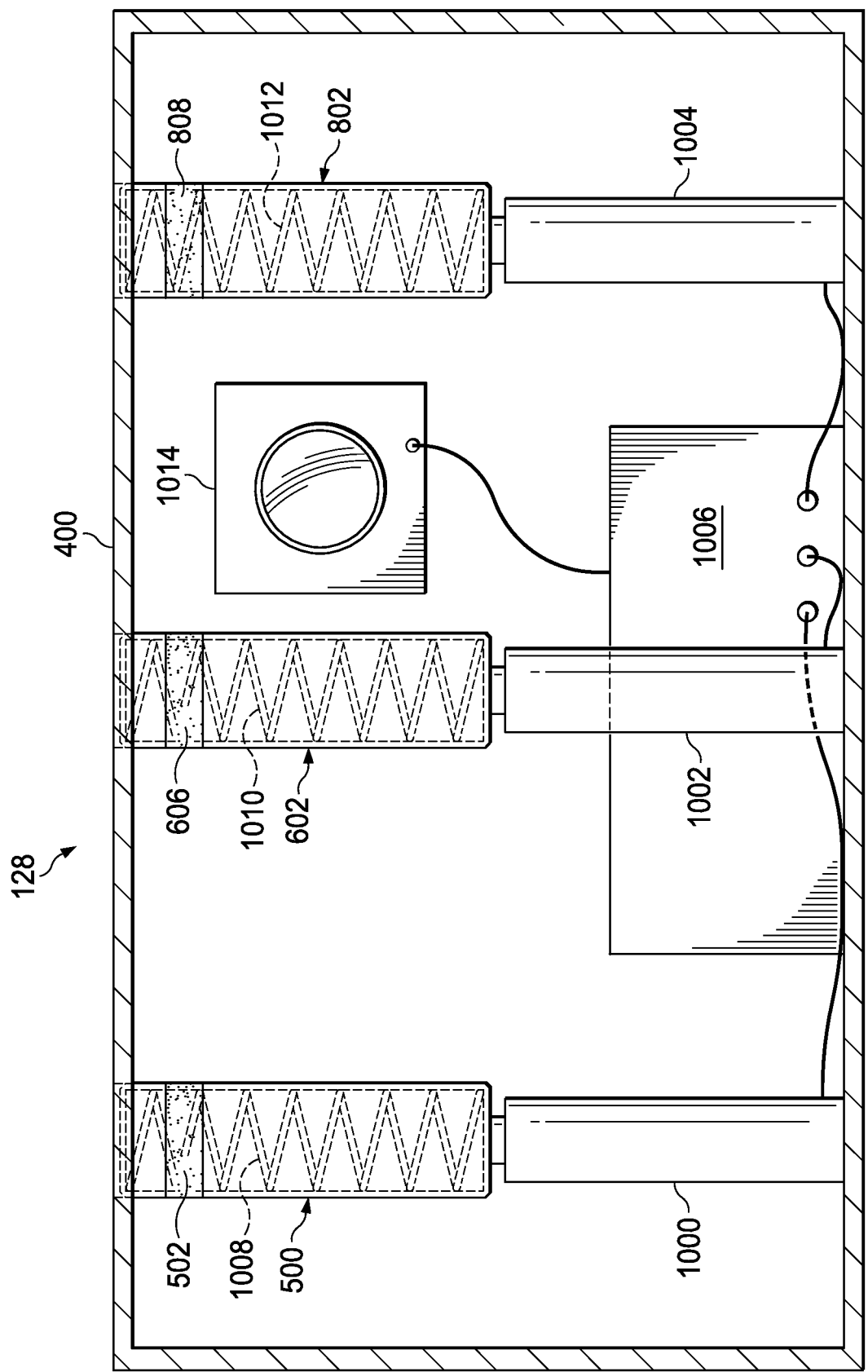
FIG. 10 is an illustration of a cross-sectional view of a sensor unit in accordance with an illustrative embodiment.

Turning now to FIG. 10, an illustration of a cross-sectional view of a sensor unit is depicted in accordance with an illustrative embodiment. In this illustrative example, a cross-sectional view of sensor unit 128 is shown taken along lines 10-10 in FIG. 4.

As depicted, probe 500 with viscous portion 502, probe 602 with viscous portion 606, and probe 802 with viscous portion 808 are shown fully retracted into the interior of housing 400. Probe 500 is operated by actuator 1000, probe 602 is operated by actuator 1002, and probe 802 is operated by actuator 1004 in these illustrative examples. Actuator 1000, actuator 1002, and actuator 1004 may be physical implementations for actuator system 306 in FIG. 3.

Actuator 1000, actuator 1002, and actuator 1004 are configured to move probe 500, probe 602, and probe 802, respectively, into the air and retract probe 500, probe 602, and probe 802 into housing 400. Actuator 1000, actuator 1002, and actuator 1004 are controlled by controller 1006. Controller 1006 may be a physical implementation for controller 312 in FIG. 3.

In this example, drop remover 1008 is associated with probe 500, drop remover 1010 is associated with probe 602, and drop remover 1012 is associated with probe 802. Drop remover 1008, drop remover 1010, and drop remover 1012 may be physical implementations for drop remover 310 in FIG. 3.

In this illustrative example, drop remover 1008, drop remover 1010, and drop remover 1012 are shown as internal coils in this example. In other illustrative examples, drop remover 1008, drop remover 1010, and drop remover 1012 may be external heaters or associated with the surface of drop remover 1008, drop remover 1010, and drop remover 1012.

In still other illustrative examples, drop remover 1008, drop remover 1010, and drop remover 1012 may be mechanical devices. These mechanical devices may be configured to scrape ice or drops of water off of the surfaces of probe 500, probe 602, and probe 802, As depicted, camera system 1014 is present in housing 400. Camera system 1014 is an example of a physical implementation for camera system 308 in FIG. 3. Camera system 1014 is configured to generate images of probe 500, probe 602, and probe 802 when at least one of probe 500, probe 602, and probe 802 is retracted in housing 400. Camera system 1014 is also operated by controller 1006 in these illustrative examples.

Figure 11:
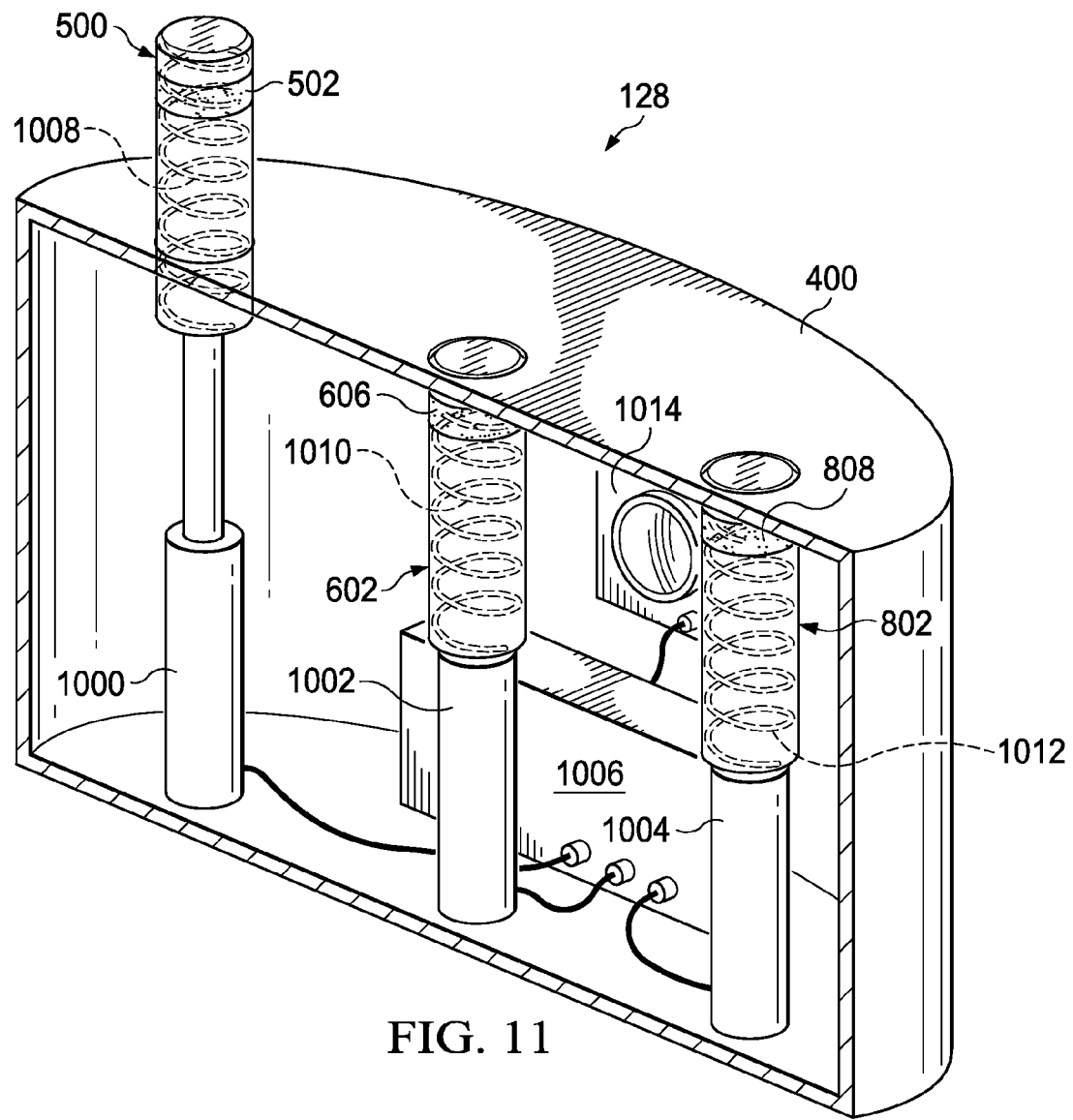
FIG. 11 is an illustration of an isometric view of a sensor unit in accordance with an illustrative embodiment.

Turning now to FIG. 11, an illustration of an isometric view of a sensor unit is depicted in accordance with an illustrative embodiment. In this example, sensor unit 128 is shown such that probe 500, probe 602, probe 802, and the components in housing 400 are visible.

In this view, actuator 1000 has extended probe 500 into the air. Viscous portion 502 is collecting drops of water in this illustrative example. Probe 602 and probe 802 remain in the interior of housing 400.

The illustrations of sensor unit 128 in FIG. 1, and FIGS. 4-11 are not meant to imply limitations to the manner in which sensor unit 300 may be implemented. For example, other sensor units may have other numbers of probes other than the three probes shown for sensor unit 128. For example, a sensor unit may include only a single probe, four probes, or some other suitable number of probes. Further, the probes also may have other shapes. For example, a probe may have a cross section that is oval, rectangular, square, hexagonal, or some shape other than the circular shape shown for probe 500, probe 602, and probe 802.

Figure 12:
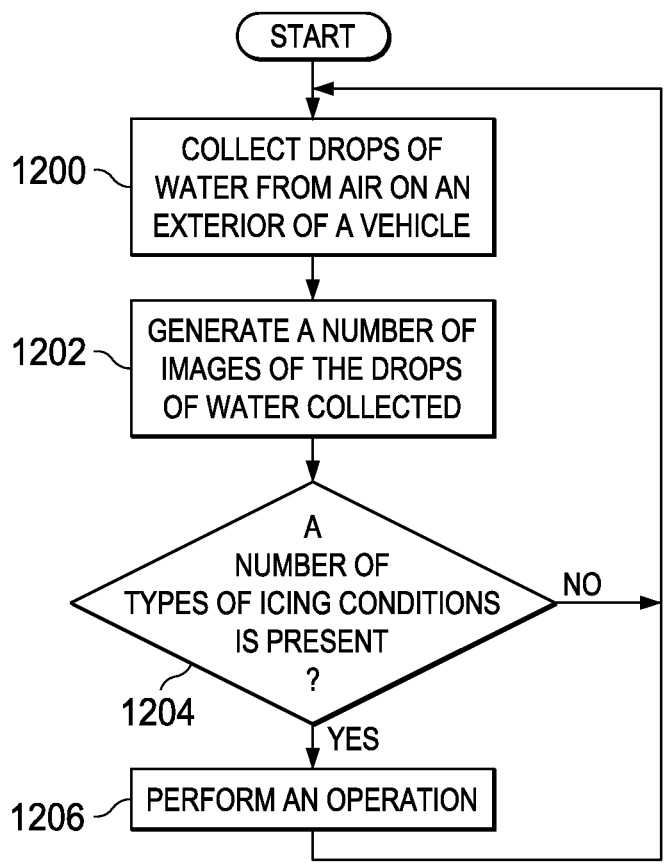
FIG. 12 is an illustration of a flowchart of a process for detecting an icing condition in accordance with an illustrative embodiment.

Turning now to FIG. 12, an illustration of a flowchart of a process for detecting an icing condition is depicted in accordance with an illustrative embodiment. The process illustrated in FIG. 12 may be implemented in icing condition detection environment 200 in FIG. 2. In particular, this process may be implemented using icing condition detection system 204.

The process begins by collecting drops of water from air on an exterior of a vehicle (operation 1200). A number of images of the drops of water collected are generated (operation 1202). The process then determines whether a number of types of icing conditions is present using the number of images (operation 1204).

If a number of types of icing conditions is present, an operation is performed (operation 1206) with the process then returning to operation 1200. If a number of types of icing conditions is not present, the process also returns to operation 1200. This process may be repeated as long as monitoring for one or more icing conditions is desired.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 13:
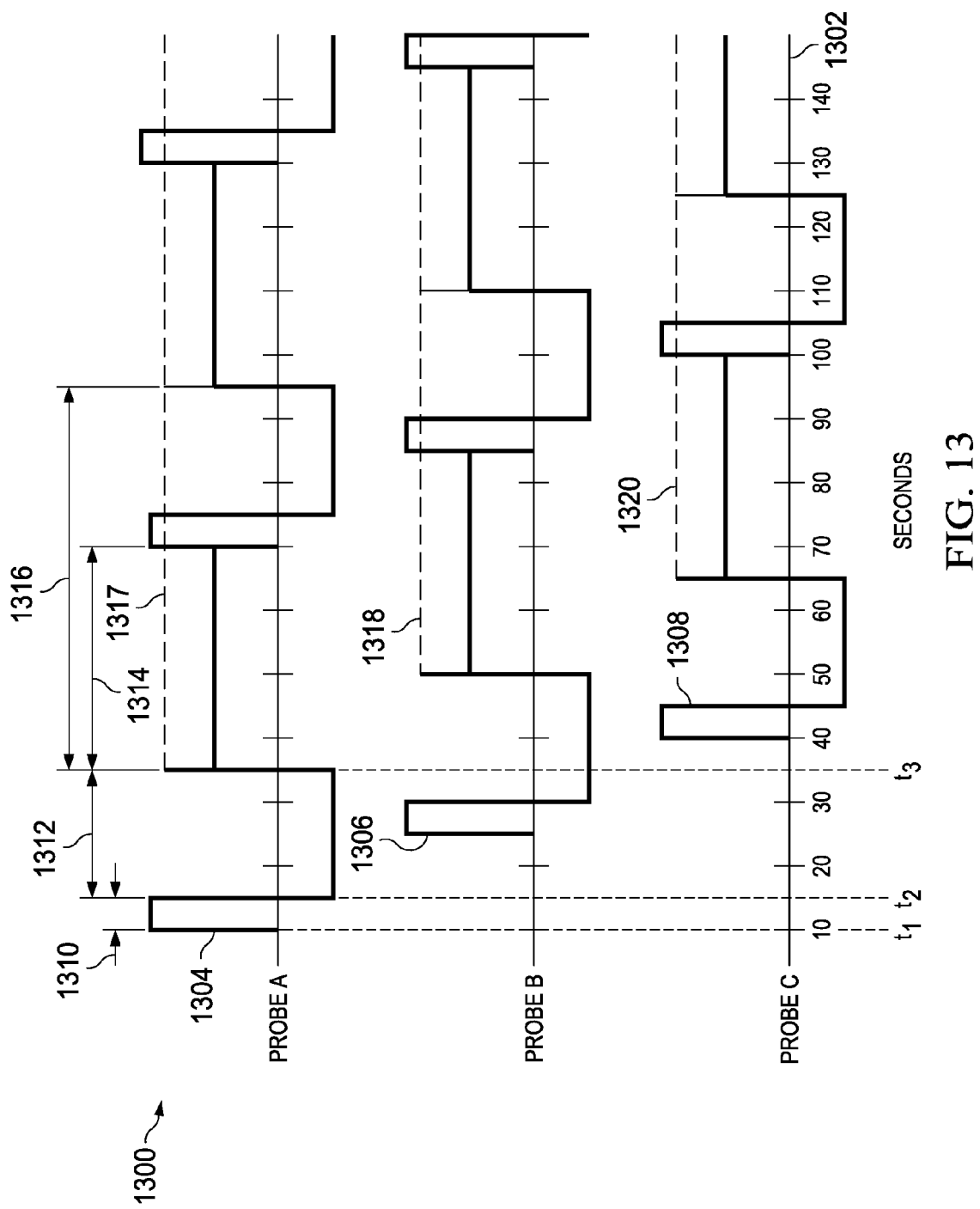
FIG. 13 is an illustration of a timing diagram for detecting a number of types of icing conditions in accordance with an illustrative embodiment.

Turning now to FIG. 13, an illustration of a timing diagram for detecting a number of types of icing conditions is depicted in accordance with an illustrative embodiment. In this illustrative example, timing diagram 1300 shows the timing of a cycle of movement of the probes in sensor unit 128 in FIGS. 4-11. Timing diagram 1300 includes scale 1302 with elapsed time measured in seconds.

As depicted, timing diagram 1300 includes line 1304, line 1306, and line 1308. Line 1304 tracks the movement over time of "probe A," line 1306 tracks the movement over time of "probe B," and line 1308 tracks the movement over time of "probe C." Probe A may correspond to probe 500, probe B may correspond to probe 602, and probe C may correspond to probe 802 in FIGS. 4-11.

In this illustrative example, the cycle time for probe A depicted by line 1304 consists of five seconds in the air stream to sample drops of water in the air during time period 1310, 20 seconds inside the housing to photograph and measure the drops during time period 1312, and 35 seconds to heat or otherwise remove the drops of water from the probe during time period 1314. After the photograph of probe A is taken, an icing measurement signal is latched for sixty seconds as shown during time period 1316. A latched signal may be a signal that is continuously transmitted. The signal may be latched in order to minimize nuisance cycling of ice protection systems. The cycle during time period 1310, time period 1312, and time period 1314 may repeat for any number of times for probe A.

In this depicted example, line 1317 indicates the signal being sent by probe A in sensor unit 128. This signal may be sent to the flight deck of the aircraft or to other suitable locations to be used in initiating operation of an anti-icing system or other suitable anti-icing measures. This signal may be sent continuously between cycles of probe A.

As depicted, probe B follows the same cycle as probe A but the cycle is offset by 15 seconds. Line 1306 shows the collection, image generation, and drop removal portions of this cycle over time. Line 1318 indicates a signal being sent to the flight deck from probe B in sensor unit 128.

In this example, probe C also follows the same cycle as probe A and probe B. The cycle time for probe C depicted by line 1306 is delayed by 30 seconds in this illustrative example. Line 1320 indicates a signal being sent to the flight deck from probe C.

In this manner, sensor unit 128 continuously provides information to the flight deck about icing conditions for the aircraft. As a result, the aircraft may prevent or remove ice, water, or both ice and water from the surface of the aircraft in substantially real time such that the aircraft operates as desired when icing conditions are present.

Thus, the illustrative embodiments provide a method and apparatus for detecting different types of icing conditions. With the use of an illustrative embodiment, the icing condition detection system may differentiate between types of icing conditions. Thus, the illustrative embodiments provide more-detailed information about icing conditions than currently used icing detection systems that are unable to differentiate between normal and supercooled large drop icing conditions.

Further, the illustrative embodiments can accurately measure drop size. These measurements may be made by comparing images of the drops of water collected on the probes to images stored in a database. Moreover, the illustrative embodiments may be operated using less power than currently used icing detection systems. For example, the sensor unit may be placed on "stand-by" until icing conditions are present.

Additionally, with the use of an illustrative embodiment, aircraft operators do not have to rely on the temperature of the aircraft to determine icing conditions. As ice accumulates on the probe, the icing condition detection system analyzes and classifies the type of icing condition present in the environment around the aircraft. This process alerts the flight deck of icing conditions much more quickly than using other techniques and provides real time updates of the icing conditions surrounding the aircraft.

The description of the different illustrative embodiments has been presented for purposes of illustration and description, and is not intended to be exhaustive or limited to the embodiments in the form disclosed. Many modifications and variations will be apparent to those of ordinary skill in the art.

Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising: a sensor system comprising a number of probes each having a viscous portion configured to collect drops of water from air on an exterior of an aircraft, the sensor system configured to and generate a number of images of the drops of water collected: wherein the sensor system comprises a camera system configured to generate the number of images of the drops of water collected by the number of probes, wherein the number of probes is configured to: extend into the air on the exterior of the aircraft and retract out of the air on the exterior of the aircraft into an interior of the aircraft; and an icing condition detector configured to detect a presence of a number of types of icing conditions for the aircraft using the number of images from the sensor system and analyze the number of images to identify a first type of icing condition and a second type of icing condition for the aircraft when the drops of water collected are frozen drops of water by comparing a size of the frozen drops of water in the number of images with a drop database of drop sizes for frozen drops of water, wherein the second type of icing condition is a supercooled large drop type of icing condition.

2. The apparatus of claim 1, wherein the icing condition detector is further configured to perform an operation in response to detecting a presence of at least one of the first type of icing condition and the second type of icing condition.

3. The apparatus of claim 2, wherein the operation is selected from at least oneof generating an alert, activating an anti-icing system, generating a log entry, and sending a report.

4. The apparatus of claim 1, wherein the number of probes is configured to periodically extend into the air on the exterior of the aircraft and retract out of the air on the exterior of the aircraft.

5. The apparatus of claim 1 further comprising: a housing, wherein the camera system is located within the housing and the number of probes is configured to extend into the air on the exterior of the aircraft from the housing and retract out of the air on the exterior of the aircraft into the housing; and a motor system configured to move the number of probes to extend into the air on the exterior of the aircraft from the housing and retract out of the air on the exterior of the aircraft into the housing.

6. The apparatus of claim 1, wherein the icing condition detector is located in one of the camera system, a housing, and a computer system in the aircraft.

7. The apparatus of claim 1, wherein the first type of icing condition is caused by first drops having a first number of sizes from about 0.00465 millimeters in diameter to about 0.111 millimeters in diameter and the second type of icing condition is caused by second drops having a second number of sizes from about 0.112 millimeters in diameter to about 2.2 millimeters in diameter.

8. An icing condition detection system comprising:
a group of sensor units configured to generate information about a number of types of icing conditions outside of an aircraft, wherein a sensor unit in the group of sensor units comprises a number of probes each having a viscous portion configured to collect drops of water from air on an exterior of the aircraft and a camera system configured to generate a number of images of the drops of water collected by the number of probes, wherein the number of probes are configured to: extend into the air on the exterior of the aircraft, and retract out of the air on the exterior of the aircraft into an interior of the aircraft; and an icing condition detector configured to detect a presence of the number of types of icing conditions for the aircraft using the number of images from the camera system and analyze the number of images to identify a first type of icing condition and a second type of icing condition for the aircraft when the drops of water collected are frozen drops of water by comparing a size of the frozen drops of water in the number of images with a drop database of drop sizes for frozen drops of water, wherein the second type of icing condition is a supercooled large drop type of icing condition.

9. The icing condition detection system of claim 8 further comprising:
an anti-icing system configured to remove ice from a surface of the aircraft when the presence of the number of types of icing conditions is present.

10. A method for detecting an icing condition, the method comprising: collecting drops of water from air on an exterior of an aircraft using a number of probes each having a viscous portion; moving the number of probes to extend into the air on the exterior of the aircraft and retract out of the air on the exterior of the aircraft into an interior of the aircraft: generating, using a camera system, a number of images of the drops of water collected on the number of probes as frozen drops of water when the number of probes are retracted out of the air on the exterior of the aircraft into the interior of the aircraft; determining whether a number of types of icing conditions for the aircraft is present using the number of images from a sensor system; and analyzing the number of images to identify a first type of icing condition and a second type of icing condition for the aircraft when the drops of water collected are frozen drops of water by comparing a size of the frozen drops of water in the number of images with a drop database of drop sizes for frozen drops of water, wherein the second type of icing condition is a supercooled large drop type of icing condition.

11. The method of claim 10 further comprising: performing an operation when the number of types of icing conditions is present.

12. The method of claim 10, wherein the collecting step further comprises: melting the frozen drops of water after generating the images and prior to moving the number of probes to extend back into the air on the exterior of the aircraft.

13. The method of claim 10, wherein the determining step comprises: differentiating between the first type of icing condition and the second type of icing condition.

14. The apparatus of claim 1, wherein the sensor system further comprises: a first probe, a second probe, and a third probe, each configured to collect the drops of water from the air on the exterior of the aircraft; a motor system configured to automatically and periodically move the first probe, the second probe, and third probe to extend into the air on the exterior of the aircraft from a housing and retract out of the air on the exterior of the aircraft into the housing; the camera system located within the housing configured to generate the number of images of the drops of water collected by the first probe, the second probe, and the third probe when at least one of the first probe, the second probe, or the third probe is retracted in the housing; wherein the first probe, the second probe, and the third probe each have the viscous portion that collects the drops of water; and wherein the viscous portion is comprised of one or more of silicon rubber, polytetrafluoroethylene, an oily resin, and a waxy resin.

* * * * *